United States Patent [19]

Cotter et al.

[11] Patent Number: 4,709,056

[45] Date of Patent: Nov. 24, 1987

[54] 4,4-DIHALOHEXAHYDROPHTHALIC ANHYDRIDES AND 4-FLUOROTETRAHYDROPHTHALIC ANHYDRIDE, AND PROCESS FOR THEIR PREPARATION

[75] Inventors: Byron R. Cotter, Northvale, N.J.; Henry C. Lin, Grand Island; Joseph A. Pawlak, Cheektowaga, both of N.Y.

[73] Assignee: Occidental Chemical Corporation, Niagara Falls, N.Y.

[21] Appl. No.: 604,271

[22] Filed: May 2, 1984

Related U.S. Application Data

[63] Continuation-in-part of Ser. No. 493856, May 12, 1983, abandoned.

[51] Int. Cl.$^4$ .................... C07C 61/09; C07D 307/89
[52] U.S. Cl. ................................ 549/246; 562/507
[58] Field of Search ..................... 549/246; 562/507

[56] References Cited

U.S. PATENT DOCUMENTS

| 2,451,612 | 10/1948 | Coffman et al. | 570/154 |
| 4,302,396 | 11/1981 | Tsujimoto et al. | 562/480 X |
| 4,517,372 | 5/1985 | Tang | 549/246 |

OTHER PUBLICATIONS

Bergmann, JACS, vol. 64, (1942), pp. 176 & 177.
Strobach et al., J. Org. Chem., vol. 36, No. 6, (1971), pp. 818–820.
Skvarchenko et al., Obshchei Khimii, vol. 30, No. 11, (1960), pp. 3535–3541.
Skvarchenko, Russian Chemical Reviews, Nov. 1963, pp. 571–589.

Primary Examiner—Richard L. Raymond
Attorney, Agent, or Firm—James F. Tao; Arthur S. Cookfair

[57] ABSTRACT

4,4-dihalohexahydrophthalic anhydrides of the formula

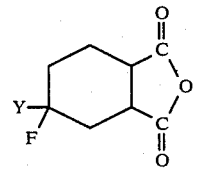

where Y is chlorine or fluorine, are prepared by the reaction of hydrogen fluoride with 4-chlorotetrahydrophthalic anhydride.

The 4,4-dihalohexahydrophthalic anhydrides of this invention can be dehydrohalogenated by reaction with basic alumina to prepare a mixture of 4-fluorotetrahydrophthalic anhydride isomers of the formula

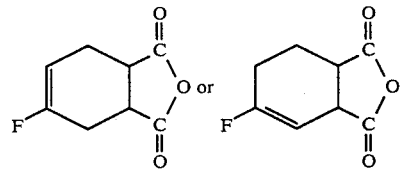

The 4-fluorotetrahydrophthalic anhydrides can then be dehydrogenated by reaction with a dehydrogenation catalyst to prepare 4-fluorophthalic anhydride.

18 Claims, No Drawings

4,4-DIHALOHEXAHYDROPHTHALIC ANHYDRIDES AND 4-FLUOROTETRAHYDROPHTHALIC ANHYDRIDE, AND PROCESS FOR THEIR PREPARATION

CROSS-REFERENCE TO RELATED APPLICATION

This is a continuation-in-part of copending application Ser. No. 493,856, filed May 12, 1983, now abandoned.

BACKGROUND OF THE INVENTION

This invention relates to novel 4,4-dihalohexahydrophthalic anhydrides of the formula

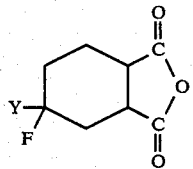

and a novel 4-fluoro-1,2,5,6-tetrahydrophthalic anhydride of the formula

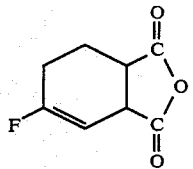

Methods for preparing and utilizing these compounds are also disclosed.

The compounds of this invention are useful as chemical intermediates for the synthesis of various end products. In particular, 4,4-dihalohexahydrophthalic anhydride and 4-fluorotetrahydrophthalic anhydride are useful in the synthesis of 4-fluorophthalic anhydride, which in turn is useful for the preparation of aromatic ether and thioether anhydride curing agents, antioxidants and polyetherimide polymers. Examples of the utility of 4-fluorophthalic anhydride and the various prior art methods for the synthesis thereof are disclosed in U.S. Pat. Nos. 3,850,965 and 3,956,321. An alternate method for synthesizing 4-fluorophthalic anhydride directly from the 4,4-dihalohexahydrophthalic anhydrides of the present invention by simultaneous dehydrohalogenation and dehydrogenation is disclosed in a commonly assigned application of David Y. Tang entitled "Process for the Preparation of 4-Fluorophthalic Anhydride", now U.S. Pat. No. 4,517,372.

The following U.S. Pat. Nos. provide further background relative to the chemistry of cyclic anhydrides and halo-substituted cyclic anhydrides: 1,891,843 to Shaw et al; 2,391,226 to Clifford et al; 2,764,597 to Barney; 3,240,792 to Patrick et al; 3,346,597 to Acetis; 3,480,667 to Siegart et al; 3,819,658 to Gormley et al; 4,045,408 to Griffith et al; and 4,302,396 to Tsujimoto et al.

The preparation of tetrahydrophthalic anhydrides and the aromatization thereof by dehydrogenation under various conditions is known in the chemical literature. Skvarchenko et al., *Obshchei Khimii*, Vol. 30, No. 11, pp. 3535–3541 disclose the aromatization of chlorosubstituted tetrahydrophthalic anhydride by heating with phosphorus pentoxide. In the aromatization process described, however, decarboxylation also occurs with the formation of the corresponding chlorosubstituted benzene compound. The preparation of tetrahydrophthalic acids and anhydrides and various methods for dehydrogenation and aromatization thereof are reviewed by Skvarchenko in *Russian Chemical Reviews*, Nov. 1963, pp. 571–589.

Bergmann, J. Amer. Chem. Soc., 64, 176 (1942) discloses the aromatization of tetrahydrophthalic anhydride products of Diels-Alder reactions. The author discloses that dehydrogenation occurs when the tetrahydrophthalic anhydride product is boiled in nitrobenzene. However, it is further disclosed that dehydrogenation does not occur when p-bromonitrobenzene, p-chloronitrobenzene, or m-dinitrobenzene in xylene is employed. Moreover, it has been found that when the dihalohexahydrophthalic anhydrides of this invention are dehydrogenated in nitrobenzene, a portion of the nitrobenzene is reduced to aniline. The aniline reacts with the anhydride group of either the starting material or product to form imides and thus lower the yield of desired product.

The preparation of 1-fluorocycloalkene from the corresponding 1,1-difluorocycloalkane by reaction with anhydrous neutral alumina is disclosed in Strobach et al., *J. Org. Chem.*, Vol. 36, pages 818–820 (1971).

The preparation of 4-fluoro-1,2,3,6-tetrahydrophthalic anhydride is disclosed in U.S. Pat. No. 2,451,612. The reference discloses that this isomer can be prepared by the reaction of fluoroprene (2-fluoro-1,3-butadiene) with maleic anhydride. The compound is reported as the hydrolyzed fluorophthalic acid.

It is a principal object of the present invention to provide novel intermediate compounds which are useful in the synthesis of 4-fluorophthalic anhydride. It is another object of this invention to provide a commercially attractive synthetic route to prepare 4-fluorophthalic anhydride.

SUMMARY OF THE INVENTION

In accordance with this invention, novel 4,4-dihalohexahydrophthalic anhydrides are prepared by reacting a 4-chlorotetrahydrophthalic anhydride with hydrogen fluoride. This reaction can be illustrated as follows

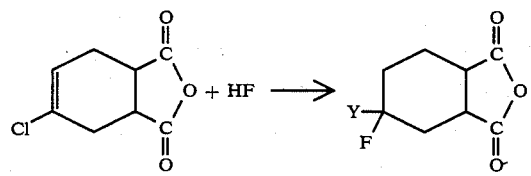

where Y is chlorine or fluorine.

The reaction actually produces a mixture of 4-chloro-4-fluorohexahydrophthalic anhydride and 4,4-difluorohexahydrophthalic anhydride. The relative proportion of each compound depends on the degree of fluorination of the substrate. Either or both of these compounds can be heated in the presence of an effective amount of basic alumina to prepare an isomeric mixture of 4-fluorotetrahydrophthalic anhydrides as follows

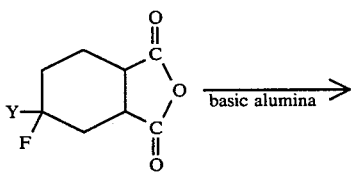

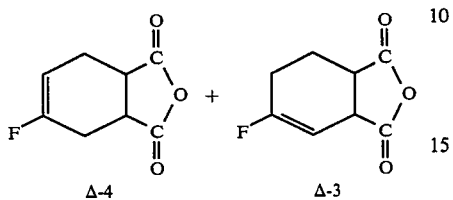

where Y is chlorine or fluorine. In this reaction, the Δ-3 isomer of 4-fluorotetrahydrophthalic anhydride is a novel compound.

Either or both of the 4-fluorotetrahydrophthalic anhydride isomers can then be aromatized by heating in the presence of a dehydrogenation catalyst to prepare 4-fluorophthalic anhydride. Suitable dehydrogenation catalysts include the nobel metals, e.g. platinum, palladium, rhodium, ruthenium, and iridium, nickel, gamma-alumina, chromium oxide, molybdenum oxide, tungsten oxide, vanadium oxide and rhenium, either supported or unsupported. The preferred catalyst system is palladium on a carbon support. The basic aromatization reaction can be illustrated as follows

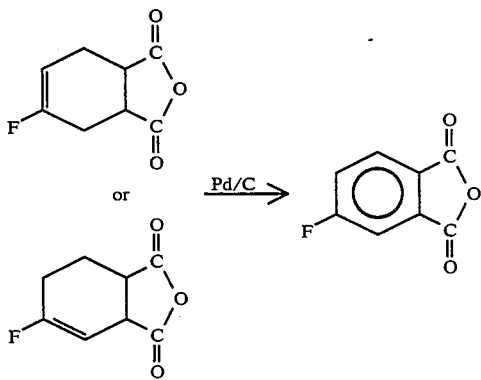

DESCRIPTION OF THE PREFERRED EMBODIMENTS

The 4,4-dihalohexahydrophthalic anhydrides of the present invention are prepared by the reaction of hydrogen fluoride with 4-chlorotetrahydrophthalic anhydride as follows

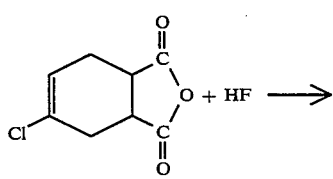

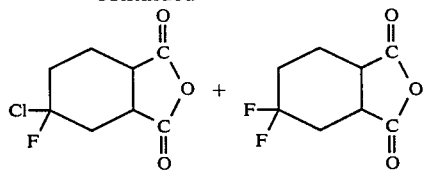

4-chlorotetrahydrophthalic anhydride, a starting material for reaction (1), is a commercially available product which can be conveniently prepared by reacting chloroprene with maleic anhydride as shown below

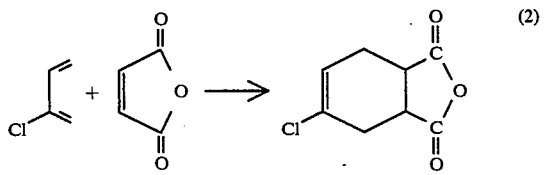

Both of the starting materials for reaction (2) are readily available through commercial sources.

Reaction (1) is suitably carried out in the liquid phase either at atmospheric pressure or under applied or autogenous pressure, at temperatures ranging from about 0° C. to about 150° C., and preferably from about 20° C. to about 70° C. The reaction rate is temperature dependent, the lower temperatures resulting in lower reaction rates.

The molar ratio of reactions, that is HF:4-chlorotetrahydrophthalic anhydride, may vary considerably and will typically be in the range of from about 1.1:1 to about 25:1. The reaction will occur at lower molar ratios, but the conversion rate will be low. Higher ratios may be employed, but are generally less economical. When it is desired to maximize the yield of 4-chloro-4-fluorohexahydrophthalic anhydride, it is preferred to utilize a ratio of HF:4-chlorotetrahydrophthalic anhydride in the range of from about 1.1:1 to about 2:1. When it is desired to maximize the yield of 4,4-difluorohexahydrophthalic anhydride, it is preferred to employ a ratio of from about 2:1 to about 25:1. If it is desired to maximize the yield of 4-chloro-4-fluorohexahydrophthalic anhydride, it is preferred to carry out the reaction in the absence of a catalyst. If it is desirable to maximize the yield of 4,4-difluorohexahydrophthalic anhydride as well as increase the conversion rate, it is preferred to run the reaction at a temperaure of 70° C. at autogenous pressures of about 60–65 psig and HF:4-chlorotetrahydrophthalic anhydride molar ratio of 8:1. The rate of reaction can also be increased by the use of a Lewis acid catalyst. Typical Lewis acid catalysts include for example aluminum chloride, antimony trichloride, antimony pentachloride, antimony trifluoride, antimony pentafluoride, antimony oxychloride, molybdenum pentachloride, ferric chloride, ferrous chloride, and the like.

The crude reaction product of hydrogen fluoride and 4-chlorotetrahydrophthalic anhydride, in accordance with the process of this invention, contains a mixture of the 4-chloro-4-fluorohexahydrophthalic anhydride and the 4,4-difluorohexahydrophthalic anhydride, the proportions of each being dependent on reaction conditions as set forth above. The anhydride products may be separated and isolated by conventional physical separation techniques, such as fractional crystallization, vacuum distillation, or the like.

The 4,4-dihalohexahydrophthalic anhydrides of this invention can be used directly to synthesize 4-fluorophthalic anhydride in accordance with a process more fully described in a commonly assigned application of David Y. Tang entitled "Process for the Preparation of 4-Fluorophthalic Anhydride", concurrently filed herewith. Alternatively, the 4,4-dihalohexahydrophthalic anhydrides can be used to prepare 4-fluorotetrahydrophthalic anhydride, which can subsequently be used to synthesize 4-fluorophthalic anhydride as disclosed in more detail herein. The former process requires fewer processing steps but results in a lower overall product yield than the latter process. In any event, the crude reaction product of hydrogen fluoride and 4-chlorotetrahydrophthalic anhydride can be used in either of the aforesaid processes without the need for separation of individual components. Nevertheless, it is preferred to utilize the process conditions set forth hereinabove to maximize the yield of 4,4-difluorohexahydrophthalic anhydride since 4-chloro-4-fluorohexahydrophthalic anhydride may yield some 4-chlorophthalic anhydride in subsequent reactions.

The 4,4-dihalohexahydrophthalic anhydrides may be hydrolyzed in a conventional manner, such as by treatment with water, to prepare the corresponding acids, that is, 4-chloro-4-fluorohexahydrophthalic acid and 4,4-difluorohexahydrophthalic acid.

The 4,4-dihalohexahydrophthalic anhydrides prepared in accordance with this invention can be heated in the presence of basic alumina to prepare an isomeric mixture of 4-fluorotetrahydrophthalic anhydrides in accordance with the following reaction

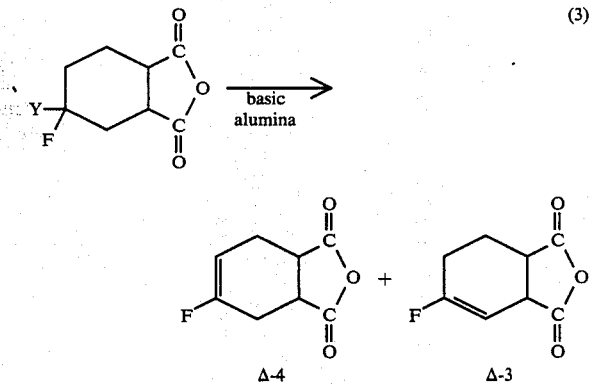

where Y is chlorine or fluorine. In reaction (3), the Δ-3 isomer of 4-fluorotetrahydrophthalic anhydride is a novel compound. In accordance with accepted nomenclature, this compound is designated as 4-fluoro-1,2,5,6-tetrahydrophthalic anhydride.

Reaction (3) is usually conducted in the liquid phase at a temperature in the range of from about 150° C. to about 270° C. A high boiling solvent such as sulfolane is usually employed. Alternatively, the reaction can be conducted in the vapor phase, suitably at a temperature of from about 200° C. to about 300° C. Atmospheric or autogenous pressure conditions can be employed in either case.

The amount of basic alumina required is generally in the range of from about 1% to about 120% by weight of reactant, and preferably from about 5% to about 25% by weight. As is known to those skilled in the art, basic alumina is a form of alumina which is devoid of significant amounts of hydrogen ions, and which can be conveniently prepared by reacting alumina with sodium hydroxide. The role of the basic alumina in the reaction is to dehydrohalogenate the 4,4-dihalotetrahydrophthalic anhydride substrate.

Separation of the isomers in the reaction product can be accomplished only with great difficulty due to the similarity of the isomers in terms of their chemical and physical properties. However, separation is generally not required or desirable in many instances.

Heating 4-fluorotetrahydrophthalic anhydride in the presence of an effective amount of a suitable dehydrogenation catalyst results in the preparation of 4-fluorophthalic anhydride. This reaction can be illustrated as follows

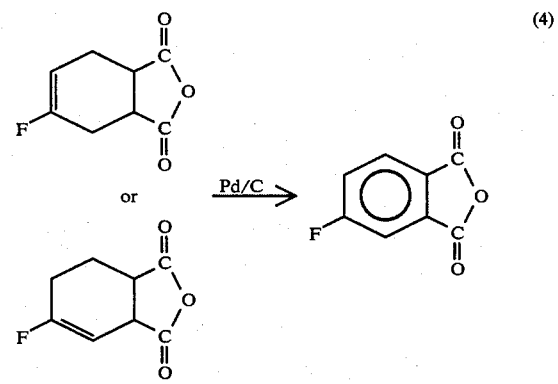

Either or both of the 4-fluorotetrahydrophthalic isomers can be used as starting materials with equal effectiveness. However, if the isomers are produced concurrently, separation entails some difficulty. Accordingly, a mixture of isomers is generally preferred.

Reaction (4) can be conducted in the liquid or vapor phase. The vapor phase reaction is preferably conducted at a temperature in the range of from about 200° C. to about 300° C. at atmospheric or reduced pressures.

If the reaction (4) is run in the liquid phase, a solvent such as 1,2,4-trichlorobenzene can be used. If an insoluble catalyst is employed, it is preferred to utilize the catalyst in finely divided form, with agitation or stirring to maintain the catalyst in dispersed form throughout the reaction medium. The process is preferably run at a temperature of between about 150° C. and about 400° C., and most preferably from about 200° C. to about 250° C. The process may be run at either atmospheric or superatmospheric conditions. If the operating temperature is below the boiling point of the reaction mixture, the reaction may be run conveniently at atmospheric pressure. However, if an operating temperature is selected above the boiling point of the reaction mixture, it is preferred to utilize a sealed reactor or autoclave and operate at autogenous pressures.

Dehydrogenation catalysts suitable for the process of this invention include platinum, palladium, rhodium, ruthenium, iridium, nickel, gamma-alumina, chromium oxide, molybdenum oxide, tungsten oxide, varadium oxide and rhenium, either unsupported or on a suitable support. Typical catalyst supports include for example activated carbon, charcoal, silicon carbide, silica gel, alumina, acidic silica-alumina, silica, titania, zirconia, kieselguhr, mixed rare earth oxides, carbonates, barium carbonate, barium sulfate, calcium carbonate, pumice, silica alumina mixtures, zeolites, and the like. Suitable catalytic complexes can also be used and include the M° compounds where M is Pd, Pt or Ni, and is bound in the structure by phosphine, phosphite or carbamyl ligands. Compelexes of this type are generally soluble in the reaction mixtures employed in the process of this invention. Typical complexes include tetrakis(triphenylphosphine)platinum (0); Bis[(bis(1,2-diphenylphosphino)ethane]palladium (0); Bis[bis(1,2-diphenylphosphino)benzene]palladium (0); Tetrakis(triphenylphosphine) nickel (0) and tetrakis(triphenylphosphite)-nickel (0).

The following examples are provided to further illustrate this invention and the manner in which it may be carried out. It will be understood, however, that the specific details given in the examples have been chosen for purposes of illustration and are not to be construed as a limitation on the invention. In the examples, unless otherwise indicated, all parts and percentages are by weight and all temperatures are in degrees Celsius.

Examples 1-7 illustrate the preparation of 4,4-difluorohexahydrophthalic anhydride and 4-chloro-4-fluorohexahydrophthalic anhydride.

EXAMPLE 1

A monel autoclave was charged with 47 parts of 4-chlorotetrahydrophthalic anhydride and cooled to about −30° C. 40 parts of hydrogen fluoride was added and the autoclave was sealed and heated to about 70° C. The temperature was maintained at an autogenous pressure of about 60 to 65 psig for about 5.5 hours. The HF was then vented and the reactor purged with $N_2$. The liquid reaction product was dissolved in acetone, treated with sodium bicarbonate, and the acetone removed by vacuum distillation. Analysis of the reaction product, using gas chromatographic techniques, indicated approximately 5.4 percent starting material; 91.7 percent 4,4-difluorohexahydrophthalic anhydride; 0.7 percent 4-chloro-4-fluorohexahydrophthalic anhydride; and 0.6 percent of 4,4-dichlorohexahydrophthalic anhydride.

EXAMPLES 2-3

The procedure of Example 1 was repeated except that amounts and conditions were varied as set forth in the table below:

| Example | 2 | 3 |
| --- | --- | --- |
| Reaction Temp (°C.) | 56°–57° | 55°–67° |
| Reaction Time (Hours) | 27 | 3.8 |
| Mole Ratio HF:4-chlorotetrahydrophthalic anhydride | 5:1 | 10:1 |
| Pressure (psig) | 110–200 | 90–200 |
| Product (G.C. Area %) | | |
| 4,4-difluorohexahydrophthalic anhydride | 73.9 | 83.4 |
| 4-chloro-4-fluorohexahydrophthalic anhydride | 6.4 | 6.3 |
| 4-chlorotetrahydrophthalic anhydride | 6.7 | 4.1 |
| 4,4-dichlorotetrahydrophthalic anhydride | 12.5 | 6.0 |

EXAMPLE 4

A mixture of 25.0 parts of 4-chlorotetrahydrophthalic anhydride and 0.80 parts of antimony pentachloride was charged to a reactor equipped with a cooling condenser and stirrer. The reaction mixture was maintained at atmospheric pressure and a temperature of 23° C. to 40° C. with stirring, while 39.6 parts of hydrogen fluoride was added over a period of about one hour. The reaction mixture was maintained under the same temperature and pressure conditions, with stirring for an additional 42 hours. The hydrogen fluoride was then removed by evaporation over a period of about two hours. The reaction mixture was then heated to about 65°–70° C., maintained at this temperature for about two hours, then cooled to room temperature. Analysis of the reaction product by gas chromatographic techniques indicated 83.4 percent 4,4-difluorohexahydrophthalic anhydride; 11.2 percent 4-chloro-4-fluorohexahydrophthalic anhydride; 3.6 percent 4-chlorotetrahydrophthalic anhydride.

EXAMPLES 5-7

The procedure of Example 4 was repeated except that catalyst and conditions were varied as shown in the table below:

| Example | 5 | 6 | 7 |
| --- | --- | --- | --- |
| Reaction Temp (°C.) | 24° | 24° | 24° |
| Total Reaction Time (Hours) | 23.6 | 24.5 | 23.3 |
| Catalyst | $SbCl_5$ | $MoCl_5$ | $SbF_5$ |
| (Parts) | 3.5 | 1.7 | 0.66 |
| 4-chlorotetrahydrophthalic anhydride (parts) | 79.6 | 37.3 | 18.6 |
| Hydrogen Fluoride (parts) | 40.0 | 20.0 | 10.0 |
| Mole Ratio HF:4-chlorotetrahydrophthalic anhydride | 5.0 | 5.0 | 5.0 |
| Product (G.C. Area %) | | | |
| 4,4-difluorohexahydrophthalic anhydride | 13.1 | 15.0 | 22.8 |
| 4-chloro-4-fluorohexahydrophthalic anhydride | 34.1 | 26.9 | 42.0 |
| 4-chlorotetrahydrophthalic anhydride | 42.4 | 41.1 | 27.9 |
| Other unidentified products | 9.9 | 16.1 | 7.0 |

Examples 8 and 9 illustrate the reaction of 4,4-difluorohexahydrophthalic anhydride with basic alumina in the presence of palladium or carbon. The reaction was conducted in the liquid phase using a 1,2,4-trichlorobenzene solvent. The reaction product contains some 4-fluorophthalic anhydride in addition to 4-fluorotetrahydrophthalic anhydride due to the presence of palladium in the reaction mixture.

EXAMPLE 8

A 3-neck flash equipped with a nitrogen inlet, an air cooled condenser, a thermometer and a magnetic stirrer was charged with 5.0 grams of 4,4-difluorohexahydrophthalic anhydride, 0.50 grams of basic alumina, 20.05 grams of 1,2,4-trichlorobenzene and 1.0 grams of 5% palladium on carbon. The contents of the flask were heated to a temperature of about 195° C. to 200° C. for 9.1 hours under a nitrogen blanket. Analysis of the reaction product, using gas chromatographic techniques, indicated approximately 42.9 percent 4-fluorotetrahydrophthalic anhydride (both isomers), 36.2 percent 4-fluorophthalic anhydride, 2.3 percent starting material, and 18.6 percent of other compounds.

EXAMPLE 9

The procedure of Example 8 was repeated except that the contents of the flask were changed by decreasing the relative proportion of basic alumina to starting material. The contents of the flask were as follows: 1.5 grams of 4,4-difluorohexahydrophthalic anhydride, 0.08 grams of basic alumina, 3.0 grams of 5 percent palladium on carbon, and 15.0 grams of 1,2,4-trichlorobenzene. The flask was heated to a temperature of about 195° C. to 200° C. for 9.0 hours under a nitrogen blanket. Analysis of the reaction product, using gas chratographic techniques, indicated approximately 12.6 percent 4-fluorotetrahydrophthalic anhydride, 47.2 percent 4-fluorophthalic anhydride, 36.0 percent starting material and 4.2 percent of other compounds.

What is claimed is:

1. A 4,4-dihalotetrahydrophthalic anhydride of the formula

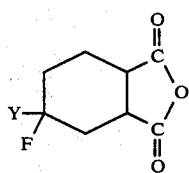

where Y is chlorine or fluorine.

2. The compound of claim 1 wherein Y is chlorine.

3. The compound of claim 1 wherein Y is fluorine.

4. A 4,4-dihalocyclohexanedicarboxylic acid of the formula

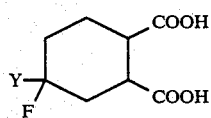

where Y is chlorine or fluorine.

5. The compound of claim 4 wherein Y is chlorine.

6. The compound of claim 4 wherein Y is fluorine.

7. A process for the preparation of 4,4-dihalohexahydrophthalic anhydrides of the formula

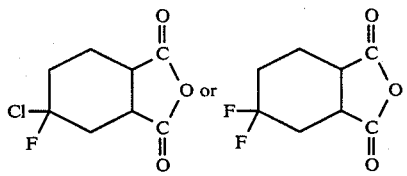

which comprises reacting hydrogen fluoride with 4-chlorotetrahydrophthalic anhydride of the formula

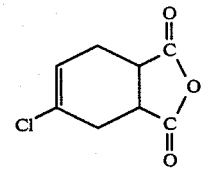

8. The process of claim 7 wherin the molar ratio of HF: 4-chlorotetrahydrophthalic anhydride is from about 1.1:1 to about 25:1.

9. The process of claim 8 wherein the molar ratio of HF: 4-chlorotetrahydrophthalic anhydride is from about 2:1 to about 25:1.

10. The process of claim 7 which is conducted in the liquid phase at a temperature of from about 0° C. to about 150° C.

11. The process of claim 10 which is conducted in the liquid phase at a temperature of from about 20° C. to about 70° C.

12. The process of claim 7 which is conducted at about atmospheric pressure.

13. The process of claim 7 which is conducted at autogenous pressure.

14. The process of claim 7 which is conducted in the presence of a Lewis Acid catalyst.

15. The process of claim 14 wherein the catalyst is antimony pentafluoride.

16. The process of claim 14 wherein the catalyst is antimony pentachloride.

17. The process of claim 14 wherein the catalyst is molybdenum pentachloride.

18. 4-fluoro-1,2,5,6-tetrahydrophthalic anhydride.

* * * * *